(12) United States Patent
Kutsuna

(10) Patent No.: US 12,350,032 B2
(45) Date of Patent: Jul. 8, 2025

(54) MEDICAL IMAGE PROCESSING APPARATUS, METHOD OF MEDICAL IMAGE PROCESSING, AND NONVOLATILE COMPUTER READABLE STORAGE MEDIUM STORING THEREIN MEDICAL IMAGE PROCESSING PROGRAM

(71) Applicant: CANON MEDICAL SYSTEMS CORPORATION, Otawara (JP)

(72) Inventor: Hideaki Kutsuna, Kawasaki (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 0 days.

(21) Appl. No.: 18/402,542

(22) Filed: Jan. 2, 2024

(65) Prior Publication Data

US 2024/0138700 A1 May 2, 2024

Related U.S. Application Data

(62) Division of application No. 17/819,648, filed on Aug. 15, 2022, now Pat. No. 11,896,362.

(30) Foreign Application Priority Data

Sep. 17, 2021 (JP) ................. 2021-152507

(51) Int. Cl.
*A61B 5/055* (2006.01)
*G01R 33/48* (2006.01)
(52) U.S. Cl.
CPC .............. *A61B 5/055* (2013.01); *G01R 33/48* (2013.01); *G01R 33/4826* (2013.01); *G06T 2207/10088* (2013.01)
(58) Field of Classification Search
CPC .............. A61B 5/055; G01R 33/48; G06T 2207/10088
See application file for complete search history.

(56) References Cited

U.S. PATENT DOCUMENTS

2019/0122339 A1 4/2019 Moon
2019/0336033 A1 11/2019 Takeshima
2020/0396415 A1 12/2020 Kokura

FOREIGN PATENT DOCUMENTS

JP 2019-181226 A 10/2019
JP 2020-201823 A 12/2020

OTHER PUBLICATIONS

R. Peters et al., "The Clinical Benefits of AIR™ Recon DL for MR Image Reconstruction", http://tinyurl.com/AIR-Recon-DL-whitepaper, 2020, 11 Pages.

(Continued)

*Primary Examiner* — G. M. A Hyder
(74) *Attorney, Agent, or Firm* — Oblon, McClelland, Maier & Neustadt, L.L.P.

(57) ABSTRACT

A medical image processing apparatus according to the present embodiment includes processing circuitry. The processing circuitry inputs a first magnetic resonance image reconstructed with super-resolution processing on magnetic resonance data and a second magnetic resonance image obtained by imaging the same object as that of the first magnetic resonance image and with artifacts suppressed compared with the first magnetic resonance image, to a leaned model, the learned model being configured to output a third magnetic resonance image having the same resolution as that of the first magnetic resonance image and with the artifacts suppressed, generates the third magnetic resonance image based on the first magnetic resonance image and the second magnetic resonance image, using the learned model.

14 Claims, 11 Drawing Sheets

(56) References Cited

OTHER PUBLICATIONS

Penkin et al., "Hybrid Method for Gibbs-Ringing Artifact Suppression in Magnetic Resonance Images", Programming and Computer Software, 2021, vol. 47, No. 3, pp. 207-214, XP037480104.
Extended European Search Report issued on Jan. 30, 2023 in European Patent Application No. 22190996.3, 11 pages.
Zhao et al. "Gibbs-ringing artifact suppression with knowledge transfer from natural images to MR images" Multimedia Tools and Applications (2020) vol. 79, No. 45-46, pp. 33711-33733, XP037308012.
Wang et al. "Reduction of Gibbs Artifacts in Magnetic Resonance Imaging Based on Convolutional Neural Network", 10th International Congress on Image and Signal Processing, BioMedical Engineering and Informatics, IEEE, pp. 1-5, XP033326518, (CISP-BMEI 2017).
Zhang et al. "MRI Gibbs-ringing artifact reduction by means of machine learning using convolutional neural networks" Magnetic Resonance in Medicine, 2019 vol. 82, No. 6, XP055899170, pp. 2133-2145.
Ruan et al. "Gibbs-Ringing Artifact reduction in MR images with varying sampling levels Via a Single Convolutional Neural Network" Proceedings of the International Society for Magnetic Resonance in Medicine, ISMRM $27^{th}$ Annual Meeting and Exhibition, May 11-16, 2019, No. 4856, XP040712240.
Tamada "Review: Noise and artifact reduction for MRI using deep learning" Arxiv.org, Cornell University Library 201 Olin Library Cornell University, Ithaca, NY Feb. 28, 2020, XP081610490.
Kellner et al. "Gibbs-Ringing Artifact Removal Based on Local Subvoxel-Shifts", Magnetic Resonance in Medicine vol. 76, No. 5, pp. 1574-1581 (2016), XP093246898.
Examination Report dated Feb. 12, 2025 issued in corresponding European patent application No. 22190996.3.

MEDICAL IMAGE PROCESSING APPARATUS, METHOD OF MEDICAL IMAGE PROCESSING, AND NONVOLATILE COMPUTER READABLE STORAGE MEDIUM STORING THEREIN MEDICAL IMAGE PROCESSING PROGRAM

CROSS-REFERENCE TO RELATED APPLICATIONS

This application is a division of U.S. patent application Ser. No. 17/819,648, filed on Aug. 15, 2022, which is based upon and claims the benefit of priority from Japanese Patent Application No. 2021-152507, filed on Sep. 17, 2021, the entire contents of each of which are incorporated herein by reference.

FIELD

Embodiments described herein relate generally to a medical image processing apparatus, a method of medical image processing, and a nonvolatile computer readable storage medium storing therein a medical image processing program.

BACKGROUND

Conventionally, super-resolution processing on images is known. However, when performing the super-resolution processing on magnetic resonance (hereinafter called MR) images, MR data as the original of MR images is data in the k-space, and thus conventional super-resolution processing on images is not necessarily suitable.

When the super-resolution processing is performed on the MR data in the k-space, zero padding is executed in a high-frequency region outside the MR data in the k-space. In this case, when a super-resolution MR image is reconstructed by reconstruction on the MR data with zero padding, Gibbs artifacts appear in the super-resolution MR image. The Gibbs artifacts are caused by termination of end data in the MR data in the k-space. A filter reducing the termination of the end data is applied to the original MR data in order to reduce the Gibbs artifacts. However, the application of the filter reduces the end data, and thus the effect of super-resolution may be reduced.

When the super-resolution processing is performed on an MR image, artifacts similar to the Gibbs artifacts may appear in the super-resolution MR image, depending on the super-resolution processing in an image space, that is, interpolation. For example, when the bicubic method or the Lanczos method is executed on the MR image as interpolation, the artifacts similar to the Gibbs artifacts may appear in the super-resolution MR image.

DETAILED DESCRIPTION

A medical image processing apparatus according to an embodiment includes processing circuitry. The processing circuitry inputs a first magnetic resonance image reconstructed with super-resolution processing on magnetic resonance data and a second magnetic resonance image obtained by imaging the same object as that of the first magnetic resonance image and with artifacts suppressed compared with the first magnetic resonance image, to a leaned model outputting a third magnetic resonance image having the same resolution as that of the first magnetic resonance image and with the artifacts suppressed, generates the third magnetic resonance image based on the first magnetic resonance image and the second magnetic resonance image, using the learned model.

The following describes an embodiment of a medical image processing apparatus, a magnetic resonance imaging (hereinafter called MRI) apparatus, a method of medical image processing, and a medical image processing program in detail with reference to the accompanying drawings.

Figure 1:
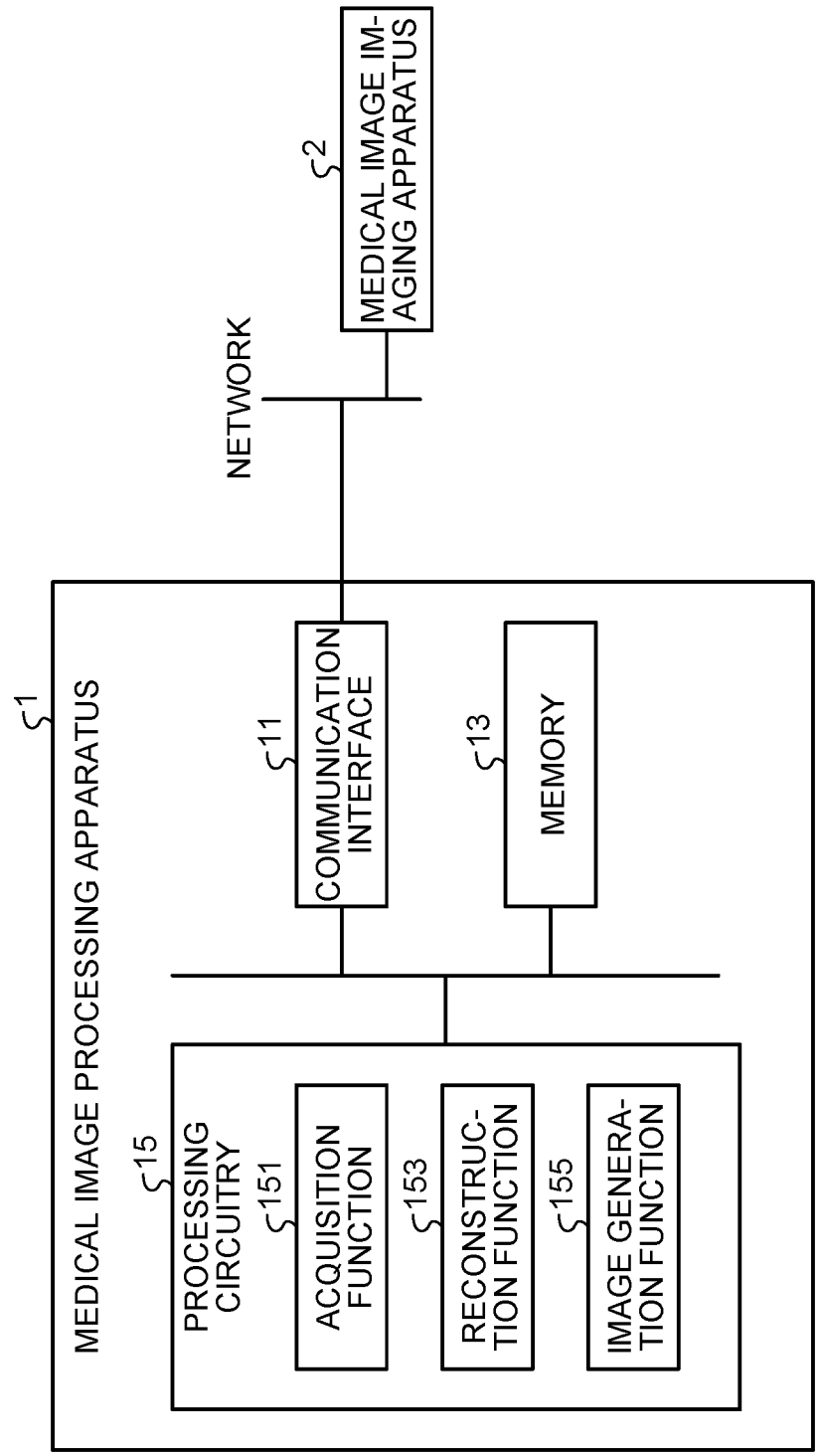
FIG. 1 is a block diagram of an example of medical image processing according to an embodiment.

FIG. 1 is a block diagram of an example of a medical image processing apparatus 1. The medical image processing apparatus 1 is installed in, for example, various modalities that can generate medical images or a server in a hospital or the like. The various functions of the medical image processing apparatus 1 may be installed in a server of picture archiving and communication systems (hereinafter PACS), a server of hospital information system (hereinafter called HIS), and the like. In this case, the medical image processing apparatus 1 is connected to various medical image imaging apparatuses 2 that can execute magnetic resonance imaging via a network. In this case, the medical image imaging apparatuses 2 correspond to conventional modalities.

The various functions installed in the present medical image processing apparatus 1 include a magnetic resonance imaging (hereinafter called MRI) apparatus, a positron emission tomography (PET)-MRI apparatus, and a single photon emission computed tomography (SPECT)-MRI apparatus, for example. To make the description specific below, it is assumed that the medical image processing apparatus 1 is installed in the MRI apparatus. In this case, the MRI apparatus will have various functions in processing circuitry 15.

Embodiment

Figure 2:
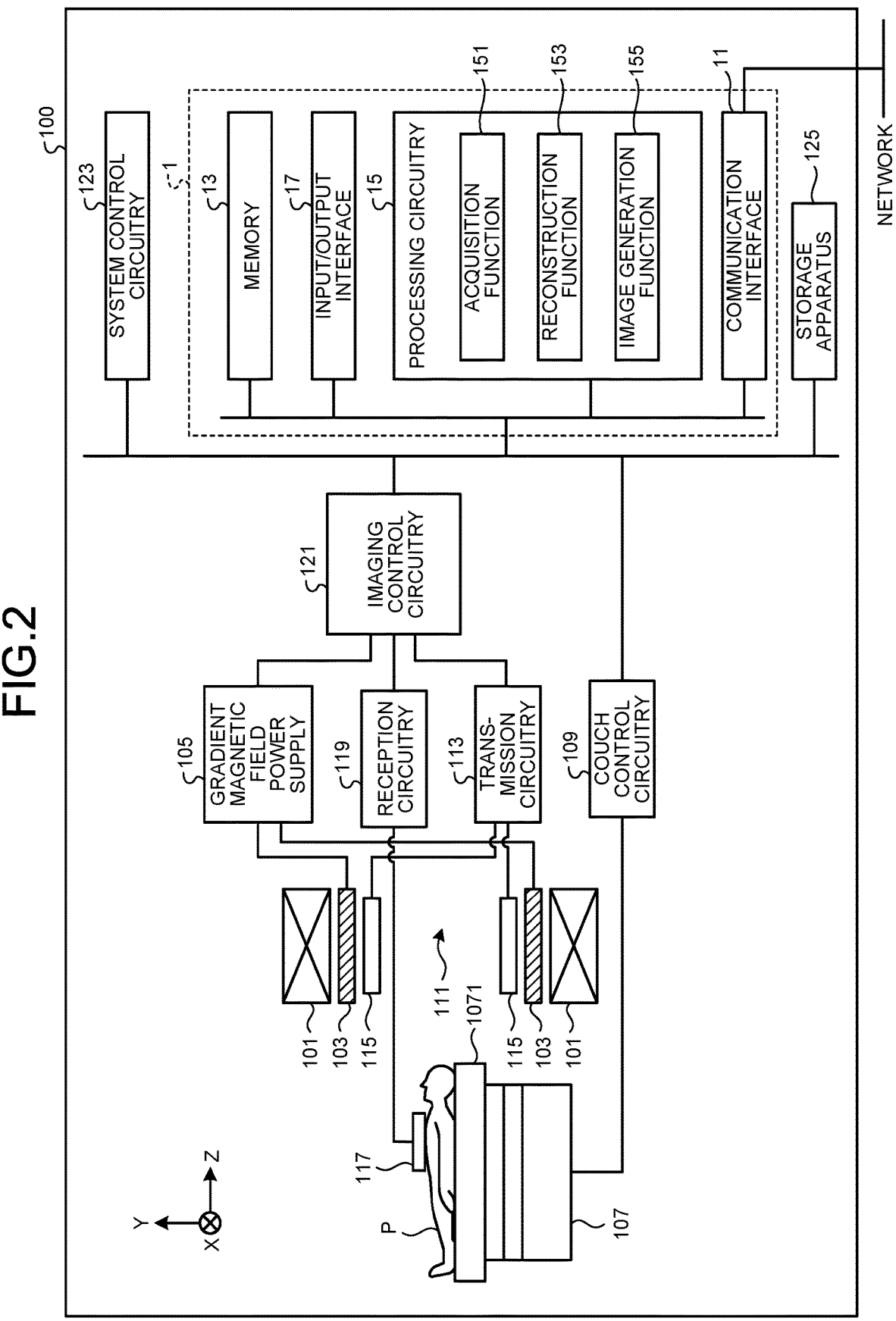
FIG. 2 is a diagram of an example of a magnetic resonance imaging apparatus according to the embodiment.

FIG. 2 is a diagram of an example of an MRI apparatus 100 according to the present embodiment. As illustrated in FIG. 2, the medical image processing apparatus 1 in the MRI apparatus 100 further has an input/output interface 17. Note that the medical image processing apparatus 1 is not necessarily installed with the input/output interface 17 as illustrated in FIG. 1. As illustrated in FIG. 2, the MRI apparatus 100 includes a static magnetic field magnet 101, a gradient coil 103, a gradient magnetic field power supply 105, a couch 107, couch control circuitry (a system controller) 109, transmission circuitry 113, a transmission coil 115, a reception coil 117, reception circuitry 119, imaging control circuitry (a collection unit) 121, system control circuitry (a system controller) 123, a storage apparatus 125, and the medical image processing apparatus 1.

The static magnetic field magnet 101 is a magnet formed in a hollow, substantially cylindrical shape. The static magnetic field magnet 101 generates a substantially uniform static magnetic field in the interior space. A superconducting magnet or the like is used as the static magnetic field magnet 101, for example.

The gradient coil 103 is a coil formed in a hollow, substantially cylindrical shape and is placed on the inner surface side of a cylindrical cooling vessel. The gradient coil 103 receives current supply individually from the gradient magnetic field power supply 105 to generate a gradient magnetic field in which the magnetic field strength changes along each of X, Y, and Z axes orthogonal to each other. The gradient magnetic field of each of the X, Y, and Z axes generated by the gradient coil 103 forms, for example, a gradient magnetic field for slice selection, a gradient magnetic field for phase encoding, and a gradient magnetic field for frequency encoding (also called a readout gradient magnetic field). The gradient magnetic field for slice selection is used to freely determine an imaging section. The gradient magnetic field for phase encoding is used to change the phase of a magnetic resonance signal (hereafter called an MR signal) in accordance with a spatial position. The gradient magnetic field for frequency encoding is used to change the frequency of the MR signal in accordance with the spatial position.

The gradient magnetic field power supply 105 is a power supply apparatus supplying a current to the gradient coil 103 under the control of the imaging control circuitry 121.

The couch 107 is an apparatus including a couchtop 1071 on which a subject P is placed. Under the control of the couch control circuitry 109, the couch 107 inserts the couchtop 1071 on which the subject P is placed into a bore 111.

The couch control circuitry 109 is circuitry controlling the couch 107. The couch control circuitry 109 drives the couch 107 under instructions by an operator via the input/output interface 17 to move the couchtop 1071 in a longitudinal direction and an up-and-down direction or, depending on cases, a right-and-left direction.

The transmission circuitry 113 supplies a high-frequency pulse modulated at a Larmor frequency to the transmission coil 115 under the control of the imaging control circuitry 121. For example, the transmission circuitry 113 has an oscillator, a phase selector, a frequency converter, an amplitude modulator, an RF amplifier, and the like. The oscillator generates an RF pulse with a resonance frequency specific to a target nucleus in a static magnetic field. The phase selector selects the phase of the RF pulse generated by the oscillator. The frequency converter converts the frequency of the RF pulse output from the phase selector. The amplitude modulator modulates the amplitude of the RF pulse output from the frequency converter in accordance with a sinc function, for example. The RF amplifier amplifies the RF pulse output from the amplitude modulator and supplies it to the transmission coil 115.

The transmission coil 115 is a radio frequency (RF) coil placed inside the gradient coil 103. The transmission coil 115 generates an RF pulse corresponding to a high-frequency magnetic field in response to the output from the transmission circuitry 113.

The reception coil 117 is the RF coil placed inside the gradient coil 103. The reception coil 117 receives the MR signal emitted from the subject P by the high-frequency magnetic field. The reception coil 117 outputs the received MR signal to the reception circuitry 119. The reception coil 117 is, for example, a coil array having one or more, typically a plurality of coil elements. To make the description specific below, the following description will be given with the reception coil 117 being the coil array having the coil elements.

The reception coil 117 may include one coil element. Although the transmission coil 115 and the reception coil 117 are described as separate RF coils in FIG. 2, the transmission coil 115 and the reception coil 117 may be implemented as an integrated transmission and reception coil. The transmission and reception coil, which corresponds to an imaging site of the subject P, is a local transmission and reception RF coil such as a head coil, for example.

The reception circuitry 119 generates a digital MR signal (hereinafter called MR data) based on the MR signal output from the reception coil 117 under the control of the imaging control circuitry 121. Specifically, the reception circuitry 119 performs various pieces of signal processing on the MR signal output from the reception coil 117 and then analog-to-digital (A/D) converts the data on which the various pieces of signal processing have been performed to generate the MR data. The reception circuitry 119 outputs the generated MR data to the imaging control circuitry 121. For example, the MR data is generated for each coil element and is output to the imaging control circuitry 121 together with a tag identifying the coil element.

The imaging control circuitry 121 collects the MR data by magnetic resonance imaging on the subject P. Specifically, the imaging control circuitry 121 controls the gradient magnetic field power supply 105, the transmission circuitry 113, the reception circuitry 119, and the like in accordance with an imaging protocol output from the processing circuitry 15 to perform imaging on the subject P. The imaging protocol has a pulse sequence in accordance with the type of an examination. The imaging protocol defines the magnitude of the current supplied to the gradient coil 103 by the gradient magnetic field power supply 105, the timing at which the current is supplied to the gradient coil 103 by the gradient magnetic field power supply 105, the magnitude and time width of the high-frequency pulse supplied to the transmission coil 115 by the transmission circuitry 113, the timing at which the high-frequency pulse is supplied to the transmission coil 115 by the transmission circuitry 113, the timing at which the MR signal is received by the reception coil 117, and the like. When receiving the MR data from the reception circuitry 119 as a result of imaging the subject P by driving the gradient magnetic field power supply 105, the transmission circuitry 113, the reception circuitry 119, and the like, the imaging control circuitry 121 transfers the received MR data to the medical image processing apparatus 1 or the like. The imaging control circuitry 121 corresponds to an imaging unit.

Although the above description describes an example in which the "processor" reads the computer program corresponding to each function from the memory 13 and executes it, the embodiment is not limited to this example. The term "processor" means circuitry such as a central processing unit (CPU), a graphics processing unit (GPU), an application specific integrated circuit (ASIC), a programmable logic device (a simple programmable logic device (SPLD) and a complex programmable logic device (CPLD), for example), and a field programmable gate array (FPGA), for example.

When the processor is the CPU, for example, the processor reads the computer program stored in the memory 13 and executes it to implement its function. On the other hand, when the processor is the ASIC, in place of storing the computer program in the memory 13, the function concerned is directly incorporated into the processor's circuitry as logic circuitry. Each processor of the present embodiment is not limited to being configured as single circuitry for each processor, and a plurality of pieces of independent circuitry may be combined to form one processor to implement its function. Although the above describes single storage circuitry storing the computer program corresponding to each processing function, a plurality of pieces of storage circuitry may be placed in a distributed manner, and the processing circuitry may read a corresponding computer program from individual storage circuitry.

The system control circuitry 123 has a processor and memories such as a read-only memory (ROM) and a random access memory (RAM) not illustrated as hardware resources and controls the MRI apparatus 100 by a system control function. Specifically, the system control circuitry 123 reads a system control program stored in the storage apparatus 125, expands it on the memory, and controls each circuitry of the MRI apparatus 100 in accordance with the expanded system control program.

For example, the system control circuitry 123 reads the imaging protocol from the storage apparatus 125 based on imaging conditions input by the operator via the input/output interface 17. The system control circuitry 123 transmits the imaging protocol to the imaging control circuitry 121 to control imaging on the subject P. The system control circuitry 123 is implemented by the processor, for example. The system control circuitry 123 may be incorporated into the processing circuitry 15. In this case, the system control function is executed by the processing circuitry 15, and the processing circuitry 15 functions as an alternative to the system control circuitry 123.

The storage apparatus 125 stores therein various computer programs executed by the system control circuitry 123, various imaging protocols, imaging conditions including a plurality of imaging parameters that define the imaging protocols, and the like. The storage apparatus 125 is, for example, a semiconductor memory element such as a RAM or a flash memory, a hard disk drive (HDD), a solid state drive (SSD), an optical disc, and the like. The storage apparatus 125 may be a compact disc (CD)-ROM drive, a digital versatile disc (DVD) drive, or a drive apparatus that reads and writes various information from and into a portable storage medium such as a flash memory. The data stored in the storage apparatus 125 may be stored in the memory 13. In this case, the memory 13 functions as an alternative to the storage apparatus 125.

The medical image processing apparatus 1 has a communication interface 11, the memory 13, and the processing circuitry 15. As illustrated in FIG. 1 and FIG. 2, in the medical image processing apparatus 1, the communication interface 11, the memory 13, and the processing circuitry 15 are electrically connected to each other with a bus. As illustrated in FIG. 1 and FIG. 2, the medical image processing apparatus 1 is connected to a network via the communication interface 11. To the network, various modalities or information processing systems in medical institutions such as HIS and radiology information system (RIS), for example, are connected in a mutually communicable manner. The medical image processing apparatus 1 illustrated in FIG. 1 may have an input interface for receiving input of various instructions by the operator, a display (an output interface) for displaying medical images generated by a generation function 157, and the input/output interface 17 as illustrated in FIG. 2.

The communication interface 11 performs data communication with various modalities that image the subject P in an examination on the subject P, HIS, PACS, and the like, for example. The standard of communication between the communication interface 11 and the various modalities and the hospital information system may be any standard; examples thereof include health level 7 (HL7), digital imaging and communications in medicine (DICOM), and both of them.

The memory 13 is implemented by the storage circuitry storing therein various types of information. For example, the memory 13 is a storage apparatus such as an HDD, an SSD, or an integrated circuitry storage apparatus. The memory 13 corresponds to a storage unit. Apart from the HDD, the SSD, and the like, the memory 13 may be a semiconductor memory element such as a random access memory (RAM) or a flash memory, an optical disc such as a compact disc (CD) or a digital versatile disc (DVD), a portable storage medium, or a drive apparatus that reads and writes various information from and into the semiconductor memory element such as the RAM.

The memory 13 stores therein an acquisition function 151, a reconstruction function 153, and an image generation function 155, which are implemented by the processing circuitry 15, in the form of a computer program executable by a computer. The memory 13 stores therein various data received by the acquisition function 151 via the communication interface 11. Specifically, the memory 13 stores therein the MR data acquired from the imaging control circuitry 121 or the medical image imaging apparatus 2 by the acquisition function 151, for example. The memory 13 also stores therein magnetic resonance images (hereinafter called MR images) generated by the reconstruction function 153 and the image generation function 155.

The memory 13 also stores therein a learned model used in the image generation function 155. The learned model is implemented by a model using a neural network that has been pre-learned by deep neural network (DNN) or the like, for example. The learned model is not limited to DNN but may be implemented by other models. The learned model is a model inputting a first MR image reconstructed by executing the super-resolution processing on the MR data placed in the k-space and a second MR image having the same imaging object as that of the first MR image and with artifacts suppressed compared with the first MR image and using a neural network learned to output a third MR image having the same resolution as that of the first MR image and with the artifacts suppressed (hereafter called a super-resolution artifact suppression model).

The artifacts in the first MR image are Gibbs artifacts. The Gibbs artifacts are also referred to as termination artifacts, truncation artifacts, ringing artifacts, and the like. The first MR image, the second MR image, the third MR image, and the super-resolution artifact suppression model will be described later.

The artifacts in the first MR image may be artifacts similar to the Gibbs artifacts. The artifacts similar to the Gibbs artifacts may occur by the super-resolution processing in an image space, for example, which is the bicubic method or the Lanczos method, for example. In this case, the first MR image in which the bicubic method or the Lanczos method has been executed as the super-resolution processing on a reconstructed image reconstructed based on the MR data is input to the super-resolution artifact suppression model.

The processing circuitry 15 controls the entire medical image processing apparatus 1. The processing circuitry 15 is implemented by the processor described above or the like. The processing circuitry 15 includes the acquisition function 151, the reconstruction function 153, the image generation function 155, and the like. The processing circuitry 15 implementing the acquisition function 151, the reconstruction function 153, and the image generation function 155 corresponds to an acquisition unit, a reconstruction unit, and an image generation unit, respectively. Each function such as the acquisition function 151, the reconstruction function 153, and the image generation function 155 is stored in the memory 13 in the form of a computer program executable by a computer. The processing circuitry 15 is the processor. For example, the processing circuitry 15 reads a computer program from the memory 13 and executes it to implement the function corresponding to each computer program. In other words, the processing circuitry 15 with each computer program read will have each function such as the acquisition function 151, the reconstruction function 153, and the image generation function 155.

The processing circuitry 15 acquires the MR data collected by imaging on the subject P by the acquisition function 151. For example, as illustrated in FIG. 1, when the processing circuitry 15 is installed in a stand-alone medical image processing apparatus 1, the acquisition function 151 acquires the MR data from a modality that can execute MR imaging via the network and the communication interface 11. For example, as illustrated in FIG. 2, when the processing circuitry 15 is installed in the MRI apparatus 100, the acquisition function 151 acquires the MR data generated by the reception circuitry 119 via the imaging control circuitry 121. The acquisition function 151 stores the acquired MR data in the memory 13.

The processing circuitry 15 reconstructs the first MR image and the second MR image based on the MR data by the reconstruction function 153. Specifically, the reconstruction function 153 reconstructs the first MR image based on the MR data after the super-resolution processing. More specifically, the reconstruction function 153 executes the super-resolution processing with a first filter having a certain filter strength applied to the MR data to reconstruct the first MR image based on the MR data on which the super-resolution processing has been executed. The first filter corresponds to a weak filter reducing the strength of an end of a high-frequency region in the MR data more weakly than the filter strength of a second filter described below. The first filter may be a filter passing the MR data. In this case, the first filter corresponds to a filter substantially passing the MR data, that is, a non-filter.

The processing circuitry 15 executes zero-filling on a no-signal high-frequency region in the MR data to which the first filter has been applied in the k-space by the reconstruction function 153. The zero-filling in the k-space relates to super-resolution in the image space, that is, super-resolution in the reconstructed image, for example. The reconstruction function 153 executes Fourier transform on the MR data to which the super-resolution processing with the application of the first filter and the zero-filling has been applied to reconstruct the first MR image. The reconstruction function 153 stores the reconstructed first MR image in the memory 13.

The high-frequency region is a frequency region in which a contribution to edge information (a contour) in the first MR image is dominant, for example.

Figure 3:
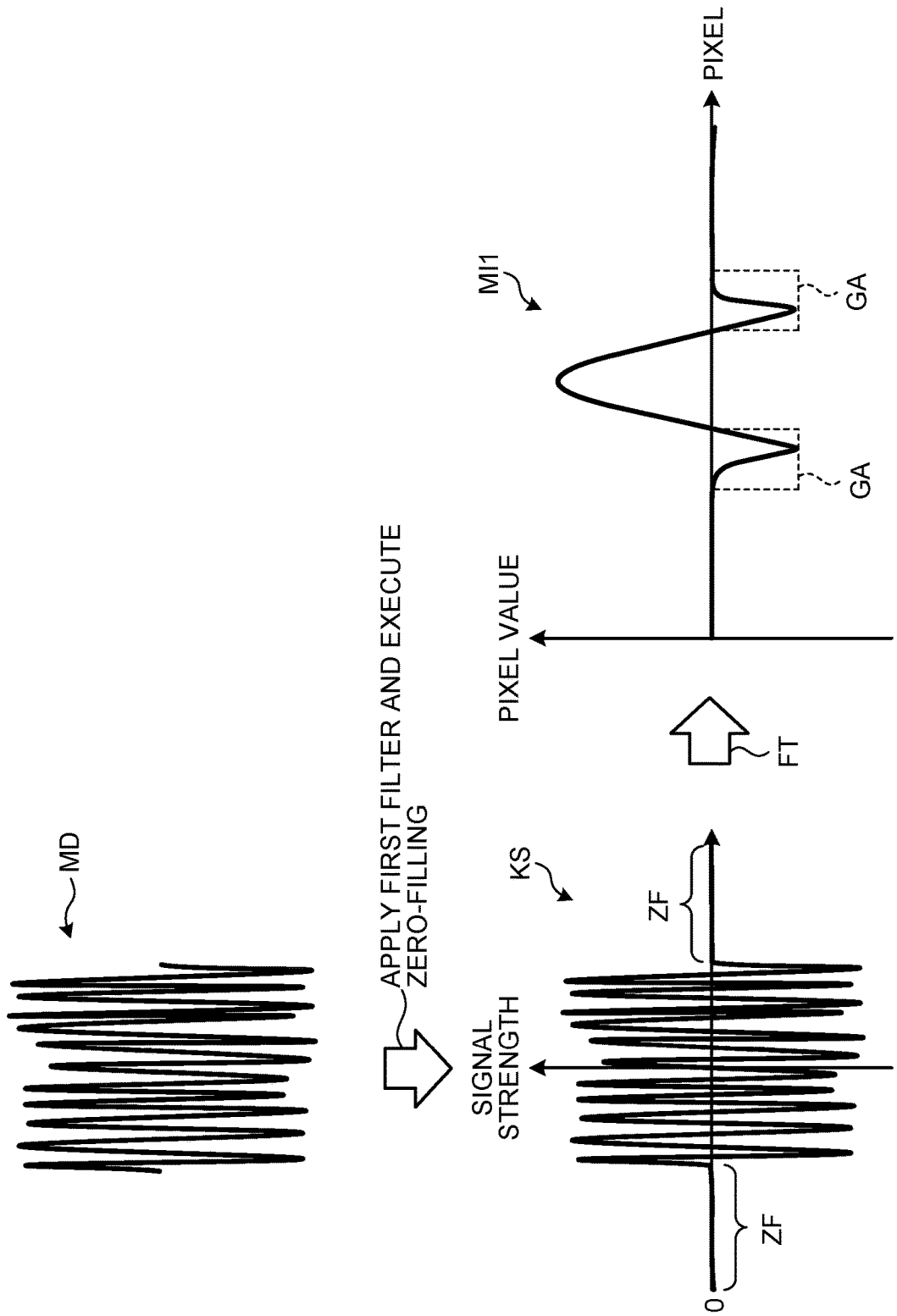
FIG. 3 is a schematic diagram of an example of an outline reconstructing a first magnetic resonance (MR) image according to the embodiment.

FIG. 3 is a schematic diagram of an example of an outline reconstructing the first MR image. FIG. 3 illustrates reconstruction with the super-resolution processing on one-dimensional MR data MD as an example. As illustrated in FIG. 3, after applying the first filter (the weak filter or the non-filter) to the one-dimensional MR data MD, the reconstruction function 153 places the MR data to which the first filter has been applied in a k-space KS with a zero-filling ZF. The reconstruction function 153 executes Fourier transform FT on the MR data to which the super-resolution processing with the application of the first filter and the zero-filling has been applied to reconstruct a first MR image MI1. The one-dimensional first MR image MI1 is a high-resolution image in which the edge information is preserved. As illustrated in FIG. 3, regions GA corresponding to the Gibbs artifact appear in the one-dimensional first MR image MI1.

The reconstruction function 153 may execute interpolation on the reconstructed image reconstructed based on the MR data as the super-resolution processing to generate the above first MR image MI1. The interpolation is interpolation in which artifacts similar to the Gibbs artifacts are likely to appear such as the bicubic method or the Lanczos method, for example. In this case, the reconstruction function 153 generates the above reconstructed image by reconstruction on the MR data before execution of the super-resolution processing.

The reconstruction function 153 reconstructs the second MR image based on the MR data so that the Gibbs artifacts occurring by reconstruction with the super-resolution processing are suppressed. As described above, the first MR image and the second MR image are images obtained by imaging the same object. That is to say, the same subject does not mean the same subject or site but means that the MR data from which the first MR image and the second MR image originate are identical. Specifically, the reconstruction function 153 executes the super-resolution processing with the second filter having a stronger filter strength than the filter strength of the first filter applied to the MR data to reconstruct the second MR image based on the MR data on which the super-resolution processing has been executed. The second filter corresponds to a strong filter reducing the strength of the end of the high-frequency region in the MR data more strongly than the filter strength of the first filter. That is to say, the second filter corresponds to a low-pass filter with a stronger filter strength than that of the first filter and has the effect of smoothing the MR data. The first filter and the second filter weaken a signal strength at the boundary between the zero-filling and the MR data to reduce the Gibbs artifacts.

The reconstruction function 153 may generate the above second MR image using interpolation in which the artifacts similar to the Gibbs artifacts are less likely to appear (bilinear interpolation, for example) on the reconstructed image reconstructed based on the MR data as the super-resolution processing. In this case, it is known that bilinear interpolation impairs image sharpness like the strong filter described above.

The reconstruction function 153 executes the zero-filling on a no-signal high-frequency region in the MR data to which the second filter has been applied in the k-space. The reconstruction function 153 executes Fourier transform on the MR data to which the super-resolution processing with the application of the second filter and the zero-filling has been applied to reconstruct the second MR image. Thus, the resolutions of the first MR image and the second MR image become the same resolution.

The resolutions of the first MR image and the second MR image become higher resolutions than that of the MR image generated by reconstructing without using the super-resolution processing on the MR data (hereinafter called a non-super-resolution image) and correspond to super-resolution against the non-super-resolution image. The reconstruction function 153 stores the reconstructed second MR image in the memory 13. The reconstruction of the first MR image and the second MR image is reconstruction with the zero-filling and is also referred to as fine reconstruction (FineRecon). FineRecon corresponds to reconstruction increasing the resolution of output.

Figure 4:
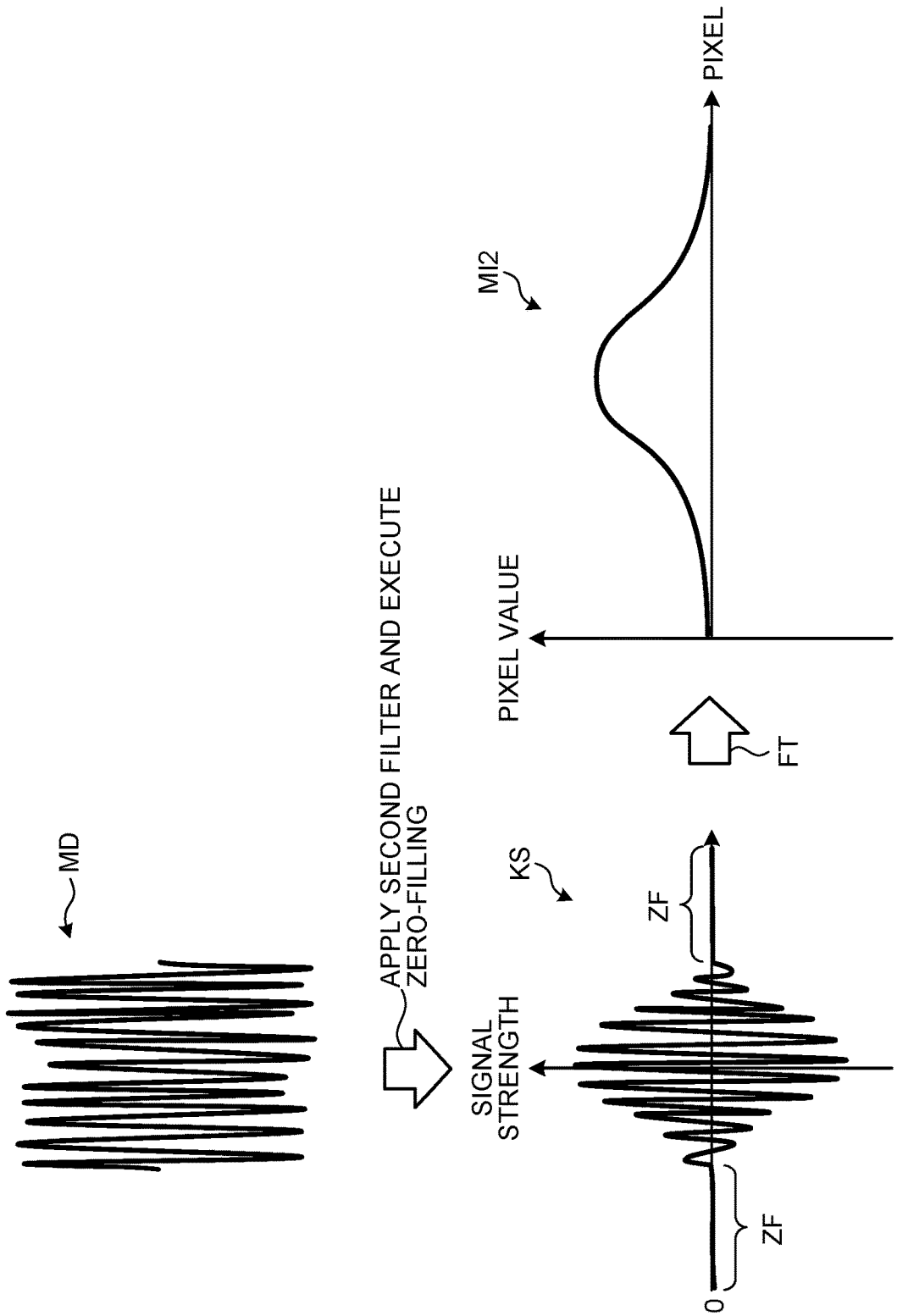
FIG. 4 is a schematic diagram of an example of an outline reconstructing a second MR image according to the embodiment.

FIG. 4 is a schematic diagram of an example of an outline reconstructing the second MR image. FIG. 4 illustrates reconstruction with the super-resolution processing on the one-dimensional MR data MD as an example. As illustrated in FIG. 4, after applying the second filter (the strong filter) to the one-dimensional MR data MD, the reconstruction function 153 places the MR data to which the second filter has been applied in the k-space KS with the zero-filling ZF. The reconstruction function 153 executes Fourier transform FT on the MR data to which the super-resolution processing with the application of the second filter and the zero-filling has been applied to reconstruct a second MR image MI2.

The one-dimensional second MR image MI2 illustrated in FIG. 4 is a blurred image with, for example, the high-frequency component suppressed by the strong filter compared with the first MR image MI1 illustrated in FIG. 3. However, in the second MR image MI2, as illustrated in FIG. 4, the Gibbs artifacts are suppressed unlike the first MR image MI1 illustrated in FIG. 3. Although FIG. 3 and FIG. 4 illustrate the one-dimensional data and images for convenience of description, they actually correspond to two-dimensional data and images. The first MR image and the second MR image are not limited to two dimensions, and are both three-dimensional images (volume data) when the MR data is three-dimensional data.

The processing circuitry 15 generates the third MR image based on the first MR image and the second MR image using the learned model (the super-resolution artifact suppression model) stored in the memory 13 by the image generation function 155. Specifically, the image generation function 155 inputs the first MR image and the second MR image to the super-resolution artifact suppression model and outputs the third MR image from the super-resolution artifact suppression model. The third MR image has the same resolution as that of the first MR image and corresponds to the super-resolution of the non-super-resolution image. In addition, the third MR image is an image with the Gibbs artifacts suppressed (reduced) comparably to the second MR image compared with the first MR image. That is to say, the third MR image corresponds to an image having a higher resolution than that of the non-super-resolution image and with the Gibbs artifacts suppressed (reduced).

Figure 5:
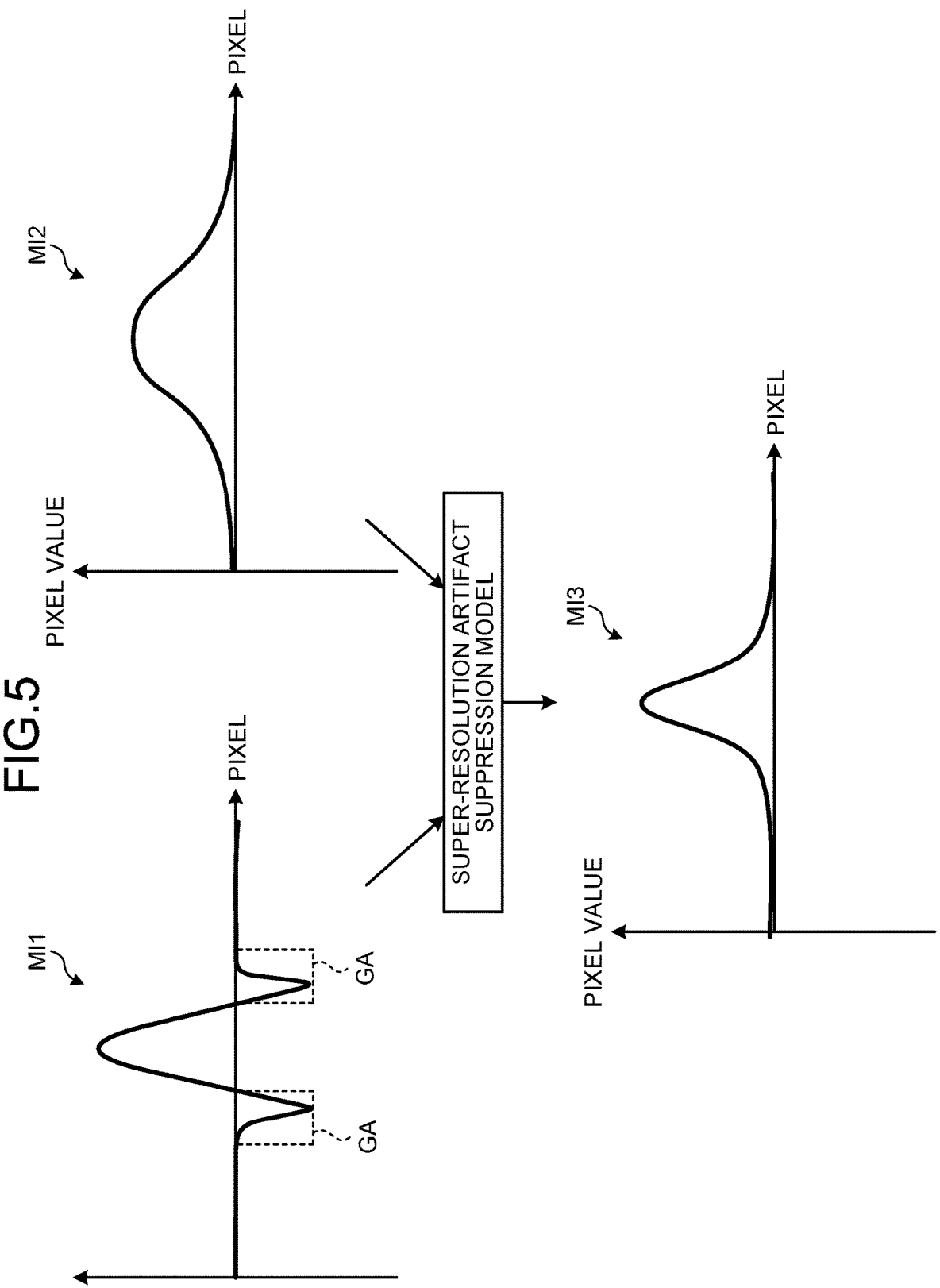
FIG. 5 is a schematic diagram of an example of an outline about generation of a third MR image corresponding to a one-dimensional super-resolution image by an image generation function according to the embodiment.

FIG. 5 is a schematic diagram of an example of an outline about generation of a third MR image MI3 corresponding to a one-dimensional super-resolution image by the image generation function 155. As illustrated in FIG. 5, the third MR image MI3 has the Gibbs artifact suppressed comparably to the second MR image MI2 compared with the first MR image MI1. In addition, the third MR image MI3 maintains the edge information (the rising edge of pixel values) comparably to the first MR image MI1 compared with the second MR image MI2.

Figure 6:
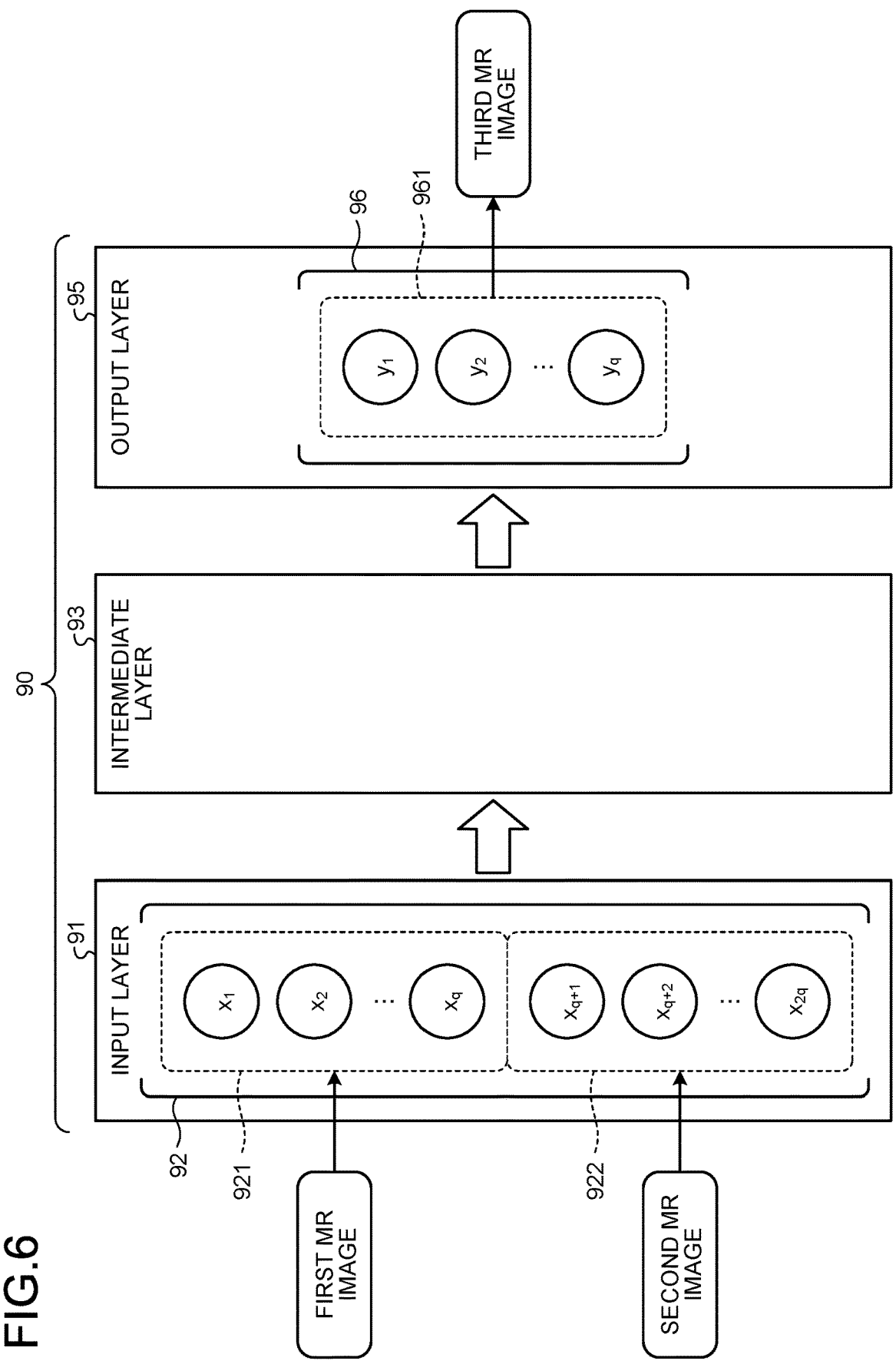
FIG. 6 is a diagram of an example of a super-resolution artifact suppression model according to the embodiment.

FIG. 6 is a diagram of an example of a super-resolution artifact suppression model 90. The super-resolution artifact suppression model 90 has an input layer 91, an intermediate layer 93, and an output layer 95. The image generation function 155 inputs the first MR image and the second MR image to the input layer 91. As illustrated in FIG. 6, the components (pixel values) of the first MR image and the second MR image are input to the input layer 91 as a single input vector 92. Where the first MR image and the second MR image both have a number of pixels of q, 2q input units are provided in the input layer 91. The input layer 91 is divided into an input unit range 921 for the first MR image and an input unit range 922 for the second MR image. In this case, a preprocessing layer or the like executing denoising processing on each of the first MR image and the second MR image may be provided before the input layer 91. The input layer 91 need not be divided into the input unit range 921 for the first MR image and the input unit range 922 for the second MR image.

Although the intermediate layer 93 illustrated in FIG. 6 is illustrated as one layer, this is not limiting; a plurality of intermediate layers may be provided between the input layer 91 and the output layer 95. A known structure can be used as appropriate for the intermediate layer 93, and thus a description thereof is omitted.

The output layer 95 illustrated in FIG. 6 outputs the third MR image. The third MR image is output from the output layer 95 in the form of a single output vector 96. The output vector 96 contains a plurality of components y. Each component y is the pixel value of each pixel in the third MR image. An output unit range 961 of the output layer 95 is limited to a range for the third MR image. The number q of the components y is equal to the number of pixels q of the first MR image and the number of pixels q of the second MR image.

Figure 7:
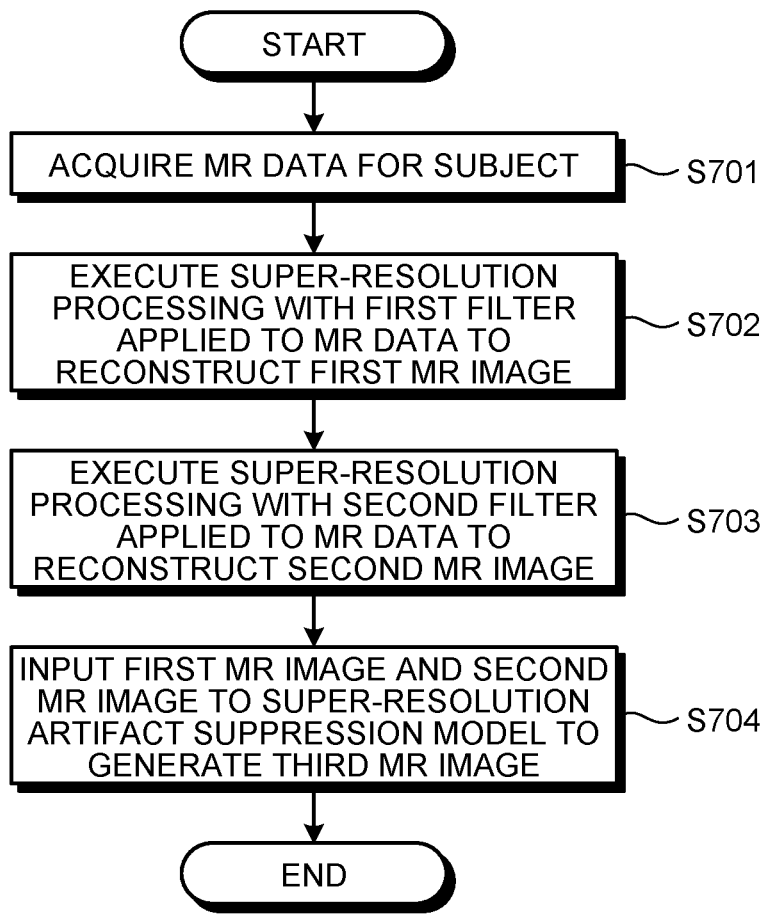
FIG. 7 is a flowchart of an example of a procedure of image generation processing generating the third MR image using the super-resolution artifact suppression model from the first MR image and the second MR image according to the embodiment.

The following describes image generation processing executed by the MRI apparatus 100 of the present embodiment configured as described above with reference to FIG. 7. FIG. 7 is a flowchart of an example of a procedure of the image generation processing generating the third MR image using the super-resolution artifact suppression model 90 from the first MR image and the second MR image.

Image Generation Processing

As a preliminary step for the image generation processing in FIG. 5, the imaging control circuitry 121 collects the MR data of the subject P by magnetic resonance imaging on the subject P.

Step S701

The processing circuitry 15 acquires the MR data generated by the reception circuitry 119 via the imaging control circuitry 121 by the acquisition function 151. The acquisition function 151 stores the acquired MR data in the memory 13. When the processing circuitry 15 is installed in the stand-alone medical image processing apparatus 1, the acquisition function 151 acquires the MR data from a modality that can execute MR imaging via the network and the communication interface 11.

Step S702

The processing circuitry 15 executes the super-resolution processing with the first filter applied to the MR data to reconstruct the first MR image by the reconstruction function 153. The reconstruction function 153 stores the reconstructed first MR image in the memory 13. The first MR image is a super-resolution image against the non-super-resolution image and has the Gibbs artifacts.

Step S703

The processing circuitry 15 executes the super-resolution processing with the second filter applied to the MR data to reconstruct the second MR image by the reconstruction function 153. The reconstruction function 153 stores the reconstructed second MR image in the memory 13. The second MR image is a super-resolution image against the non-super-resolution image and with the Gibbs artifacts suppressed. That is to say, the second MR image is an MR image with the Gibbs artifacts suppressed by the second filter in the super-resolution processing.

Step S704

The processing circuitry 15 reads the super-resolution artifact suppression model 90, the first MR image, and the second MR image from the memory 13 by the image generation function 155. The image generation function 155 inputs the first MR image and the second MR image to the super-resolution artifact suppression model 90. The image generation function 155 generates the third MR image based on the output from the super-resolution artifact suppression model 90.

The MRI apparatus 100 and the medical image processing apparatus 1 according to the embodiment described above input the first MR image reconstructed by executing the super-resolution processing on the MR data placed in the k-space and the second MR image, the image obtained by imaging the same object as that of the first MR image and with artifacts suppressed compared with the first magnetic resonance image, and using a learned model (the super-resolution artifact suppression model) 90 outputting the third MR image having the same resolution as that of the first MR image and with the artifacts suppressed, generate the third MR image based on the first MR image and the second MR image.

In this case, the MRI apparatus 100 and the medical image processing apparatus 1 according to the embodiment reconstruct the first MR image based on the MR data after the super-resolution processing and reconstruct the second MR image based on the MR data so that the artifacts occurring by reconstruction with the super-resolution processing are suppressed. Specifically, the MRI apparatus 100 and the medical image processing apparatus 1 according to the embodiment execute the super-resolution processing with the first filter applied to the MR data to reconstruct the first MR image and execute the super-resolution processing with the second filter having a stronger filter strength than the filter strength of the first filter applied to the MR data to reconstruct the second MR image.

From the above, the MRI apparatus 100 and the medical image processing apparatus 1 according to the embodiment can generate the super-resolution third MR image with the Gibbs artifacts occurring along with the super-resolution processing suppressed, that is, a high-resolution MR image with the Gibbs artifacts suppressed. From the above, the MRI apparatus 100 and the medical image processing apparatus 1 according to the embodiment can generate a super-resolution MR image with the edge information preserved and with the Gibbs artifacts effectively removed. Thus, the MRI apparatus 100 and the medical image processing apparatus 1 according to the embodiment can improve an image quality of the super-resolution image and improve diagnostic throughput about the subject P.

Modification

The difference from the embodiment is the use of the MR image without FineRecon, that is, the non-super-resolution image as the second MR image. In this case, the processing circuitry 15 executes the super-resolution processing with the first filter applied to the MR data to reconstruct the first MR image by the reconstruction function 153. The first MR image is the same as that described in the embodiment, and thus a description thereof is omitted. The reconstruction function 153 reconstructs the second MR image based on the MR data without using the super-resolution processing. The second MR image in the present modification has a lower resolution than that of the first MR image and corresponds to the non-super-resolution image in the embodiment.

The Gibbs artifacts occur strongly by the zero-filling in the super-resolution processing. Thus, the Gibbs artifacts in the second MR image in the present modification, in which the super-resolution processing is not executed, are suppressed than the Gibbs artifacts in the first MR image. That is to say, the second MR image in the present modification is the MR image having a lower-resolution than that of the first MR image and with the Gibbs artifacts originally suppressed. In other words, the second MR image in the present modification is an MR image having a lower resolution than that of the first MR image but with the Gibbs artifacts suppressed compared with the first MR image because of non execution of the super-resolution processing.

Figure 8:
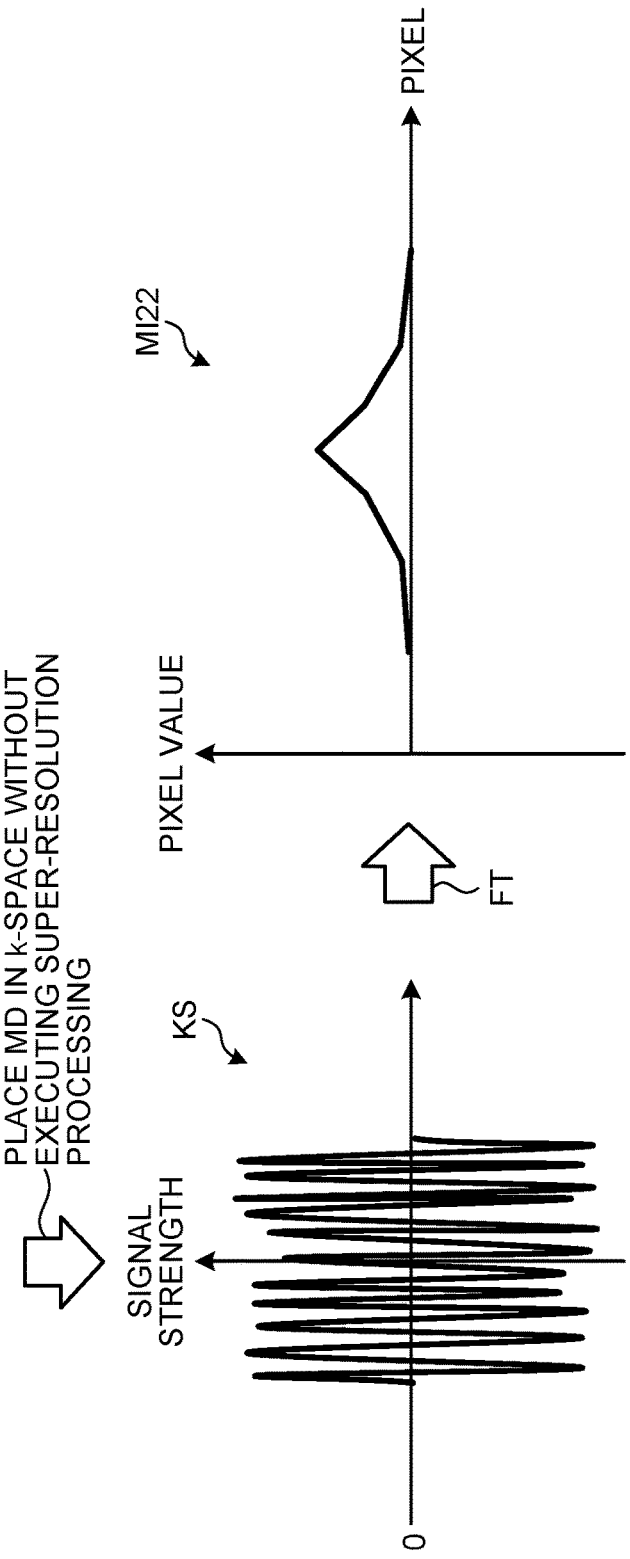
FIG. 8 is a schematic diagram of an example of an outline reconstructing the second MR image according to a modification of the embodiment.

FIG. 8 is a schematic diagram of an example of an outline reconstructing the second MR image according to the present modification. FIG. 8 illustrates reconstruction for the one-dimensional MR data MD as one example. As illustrated in FIG. 8, the reconstruction function 153 places the one-dimensional MR data MD in the k-space KS without executing the super-resolution processing with the second filter and the zero-filling applied. The reconstruction function 153 executes Fourier transform FT on the MR data MD to reconstruct a second MR image MI22.

The one-dimensional second MR image MI22 illustrated in FIG. 8 is a coarse image having fewer pixels than those of the first MR image MI1 illustrated in FIG. 3. However, as illustrated in FIG. 8, in the second MR image MI22, the Gibbs artifacts are suppressed unlike the first MR image MI1 illustrated in FIG. 3. Although FIG. 8 illustrates the one-dimensional data and image for convenience of description, they actually correspond to two-dimensional data and image. The first MR image and the second MR image are not limited to two dimensions, and are both three-dimensional images (volume data) when the MR data is three-dimensional data.

The processing circuitry 15 generates the third MR image based on the first MR image and the second MR image using the super-resolution artifact suppression model stored in the memory 13 by the image generation function 155. The super-resolution artifact suppression model in the present modification is learned separately from the embodiment, because the second MR image input to the model is different from that of the modification.

Figure 9:
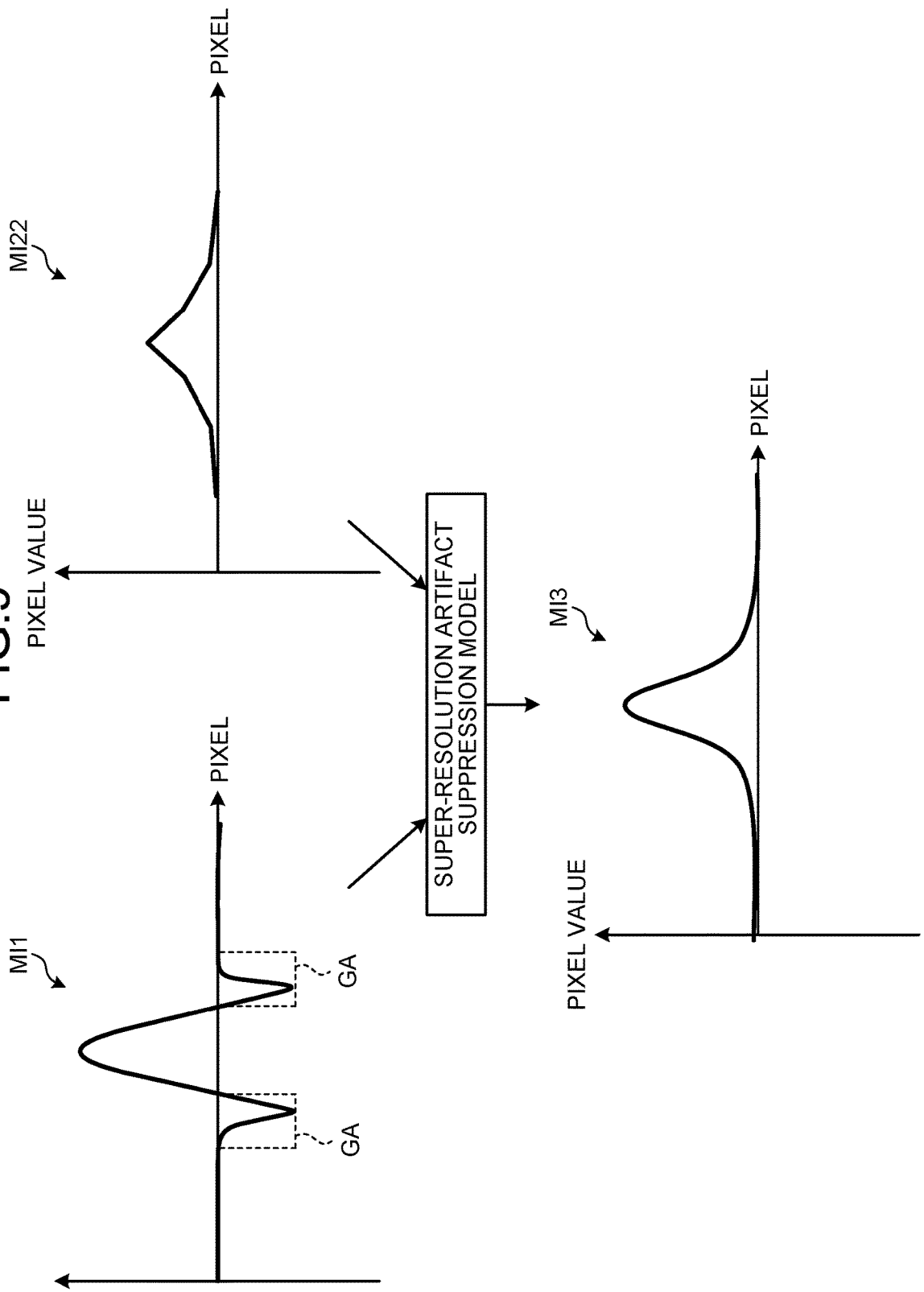
FIG. 9 is a schematic diagram of an example of an outline about generation of the third MR image corresponding to the one-dimensional super-resolution image by the image generation function according to the modification of the embodiment.

FIG. 9 is a schematic diagram of an example of an outline about generation of the third MR image MI3 corresponding to the one-dimensional super-resolution image by the image generation function 155. As illustrated in FIG. 9, the third MR image MI3 has the Gibbs artifact suppressed comparably to the second MR image MI22 compared with the first MR image MI1. In addition, the third MR image MI3 maintains the edge information (the rising edge of pixel values) comparably to the first MR image MI1 compared with the second MR image MI22. In other words, the third MR image MI3 has the Gibbs artifacts suppressed comparably to the second MR image compared with the first MR image MIL and is a super-resolution image comparable to the first MR image against the second MR image MI22.

Figure 10:
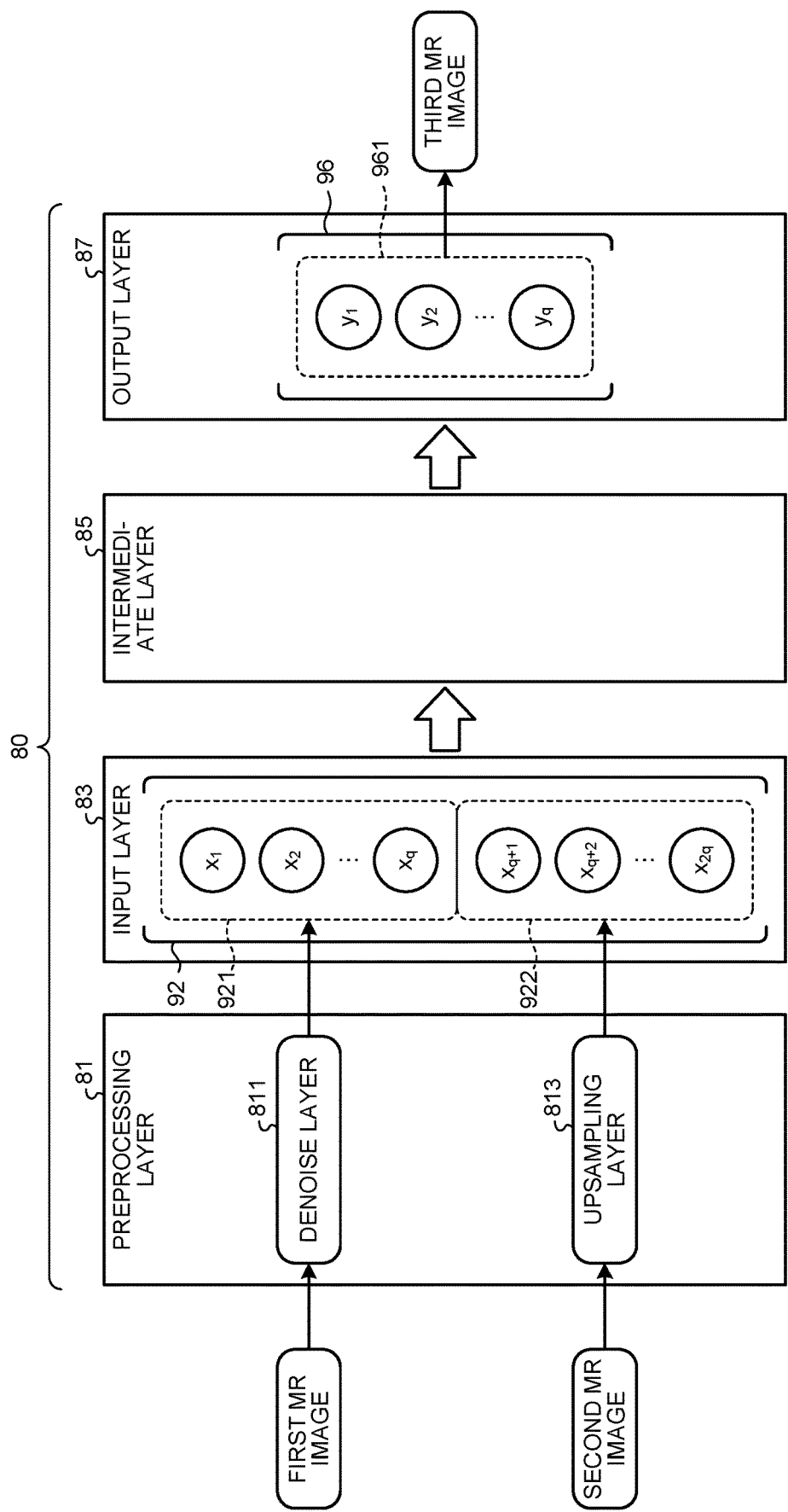
FIG. 10 is a diagram of an example of a super-resolution artifact suppression model according to the modification of the embodiment.

The following describes the super-resolution artifact suppression model in the present modification. FIG. 10 is an example of a super-resolution artifact suppression model 80 in the present modification. The super-resolution artifact suppression model 80 has a preprocessing layer 81, an input layer 83, an intermediate layer 85, and an output layer 87. The preprocessing layer 81 has a denoise layer 811 and an upsampling layer 813. The first MR image is input to the denoise layer 811. The second MR image is input to the upsampling layer 813.

The denoise layer 811 removes noise in the first MR image. As an application example of the present modification, the denoise layer 811 may be omitted. In this case, the first MR image is input to the input unit range 921 of the input layer 83.

The upsampling layer 813 upsamples the resolution of the second MR image to the resolution of the first MR image. Specifically, the upsampling layer 813, using a plurality of adjacent pixel values in the second MR image, interpolates the pixel value of a pixel between the adjacent pixel values until it matches the resolution of the first MR image. For the method of upsampling the resolution of the second MR image, that is, interpolation, known techniques can be used as appropriate, and thus a description thereof is omitted. Parameters such as weighting in the preprocessing layer 81 are adjusted as appropriate during the learning of the super-resolution artifact suppression model. For example, the preprocessing layer 81 is learned simultaneously with the artifact suppression model. The method of learning for the super-resolution artifact suppression model is not limited to the above description. For example, the preprocessing layer 81 may be learned simultaneously with the intermediate layer 93 or learned separately therefrom for practical purposes. The preprocessing layer 81 does not necessarily contain the parameters.

The input layer 83, the intermediate layer 85, and the output layer 87 are the same as those of the embodiment, and thus descriptions thereof are omitted. The parameters such as weighting in the intermediate layer 85 or the like are different from the parameters such as weighting in the intermediate layer 93 or the like of the embodiment because the data input to the input layer 83 during learning is different from that of the embodiment.

The image generation function 155 inputs the first MR image and the second MR image to the preprocessing layer 81. Specifically, the image generation function 155 inputs the first MR image to the denoise layer 811 in the preprocessing layer 81. The first MR image denoised by the denoise layer 811 is input to the input unit range 921 in the input layer 83. The image generation function 155 inputs the second MR image to the upsampling layer 813 in the preprocessing layer 81. The second MR image upsampled to the same resolution as that of the first MR image by the upsampling layer 813 is input to the input unit range 922 in the input layer 83. The other processing is the same as that of the embodiment, and thus a description thereof is omitted.

Figure 11:
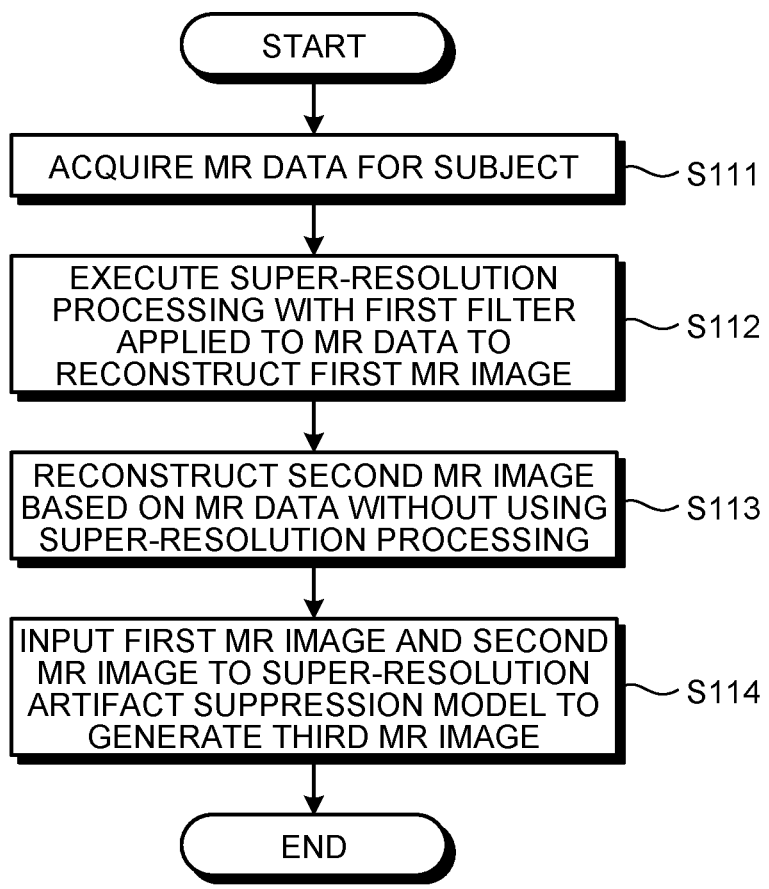
FIG. 11 is a flowchart of an example of a procedure of image generation processing generating the third MR image using the super-resolution artifact suppression model from the first MR image and the second MR image according to the modification of the embodiment.

The following describes a procedure of image generation processing according to the present modification with reference to FIG. 11. FIG. 11 is a flowchart of an example of the procedure of the image generation processing generating the third MR image using the super-resolution artifact suppression model 80 from the first MR image and the second MR image in the present modification.

Image Generation Processing

As a preliminary step for the image generation processing in FIG. 11, the imaging control circuitry 121 collects the MR data of the subject P by magnetic resonance imaging on the subject P. The processing at Step S111 and Step S112 corresponds to the processing at Steps S701 and S702, respectively, in FIG. 7, and thus descriptions thereof are omitted.

Step S113

The processing circuitry 15 reconstructs the second MR image based on the MR data without executing the super-resolution processing on the MR data by the reconstruction function 153. The reconstruction function 153 stores the reconstructed second MR image in the memory 13. The second MR image corresponds to the non-super-resolution image, and thus the Gibbs artifacts are suppressed.

Step S114

The processing circuitry 15 inputs the first MR image and the second MR image to the super-resolution artifact suppression model 80 read from the memory 13 by the image generation function 155. The super-resolution artifact suppression model 80 executes upsampling on the second MR image and outputs the third MR image based on the upsampled second MR image and the denoised first MR image. Thus, the image generation function 155 generates the third MR image based on the first MR image and the second MR image using the super-resolution artifact suppression model 80.

The MRI apparatus 100 and the medical image processing apparatus 1 according to the modification of the embodiment described above execute the super-resolution processing with the first filter having a certain filter strength applied to the MR data to reconstruct the first MR image, reconstructs the second MR image based on the MR data without using the super-resolution processing, and generates the third MR image based on the first MR image and the second MR image using the super-resolution artifact suppression model 80. The MRI apparatus 100 and the medical image processing apparatus 1 according to the present modification do not execute the super-resolution processing on the reconstruction of the second MR image and can thus shorten a processing time and improve diagnostic throughput about the subject P. The other effects are the same as those of the embodiment, and thus descriptions thereof are omitted.

To summarize the embodiment and the modification described above, the MRI apparatus 100 and the medical image processing apparatus 1 according to the embodiment and the modification generate the third MR image based on the first image and the second MR image, the MR image having the same imaging object as that of the first MR image and having a different resolution from that of the first MR image (the second MR image in the modification) or the MR image having a different frequency characteristic from that of the first MR image (the second MR image in the embodiment).

In the embodiment and the modification, the number of the MR images input to the super-resolution artifact suppression model, which corresponds to the learned model, is not limited to two. For example, in an application example combining the embodiment and the modification, the super-resolution artifact suppression model is learned so that the first MR image in the embodiment and the modification, the second MR image described in the embodiment, and the second MR image described in the modification are input, and the third MR image is output. In this case, the super-resolution artifact suppression model has the preprocessing layer 81, and the input layer 91 is provided with two input unit ranges 922 for the second MR image.

When the technical ideas in the embodiment and the modification are implemented by a method of medical image processing, the method of medical image processing inputs the first MR image reconstructed by executing the super-resolution processing on the MR data placed in the k-space and the second MR image having the same imaging object as that of the first MR image and with artifacts suppressed compared with the first MR image and, using the learned model outputting the third MR image having the same resolution as that of the first MR image and with the artifacts suppressed, generates the third MR image based on the first MR image and the second MR image. The procedure and the effects of the image generation processing related to the present method of medical image processing are the same as those described in the embodiment and the modification, and thus descriptions thereof are omitted.

When the technical ideas in the embodiment and the modification are implemented by a medical image processing program, the medical image processing program causes a computer to implement inputting the first MR image reconstructed by executing the super-resolution processing on the MR data placed in the k-space and the second MR image having the same imaging object as that of the first MR image and with artifacts suppressed compared with the first MR image and, using the learned model outputting the third MR image having the same resolution as that of the first MR image and with the artifacts suppressed, generating the third MR image based on the first MR image and the second MR image.

For example, the image generation processing can also be implemented by installing the medical image processing program in a computer in a modality such as the MRI apparatus 100, a PACS server, and the like and expanding it on the memory. In this case, the computer program that enables the computer to execute the method can be stored and distributed in a storage medium such as a magnetic disk (a hard disk or the like), an optical disc (a CD-ROM, a DVD, or the like), or a semiconductor memory. The procedure and the effects of the image generation processing by the medical image processing program are the same as those of the embodiment and the modification, and thus descriptions thereof are omitted.

At least one embodiment or the like described above can suppress the artifacts occurring along with the super-resolution processing and generate good super-resolution MR images.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

Concerning the above embodiment or the like, the following notes are disclosed as an aspect and selective features of the invention.

Note 1.

A medical image processing apparatus comprising an image generation unit configured to generate a third magnetic resonance (MR) image based on a first MR image and a second MR image, the second MR image being an MR image having the same imaging object as the imaging object of the first MR image and having a different resolution from the resolution of the first MR image or having a different frequency characteristic from the frequency characteristic of the first MR image.

Note 2.

A medical image processing apparatus comprising processing circuitry configured to input a first magnetic resonance image reconstructed with super-resolution processing on magnetic resonance data and a second magnetic resonance image obtained by imaging the same object as the object of the first magnetic resonance image and with artifacts suppressed compared with the first magnetic resonance image, to a leaned model, the leaned model being configured to output a third magnetic resonance image having the same resolution as the resolution of the first magnetic resonance image and with the artifacts suppressed, and to generate the third magnetic resonance image based on the first magnetic resonance image and the second magnetic resonance image, using the learned model.

Note 3.

The processing circuitry may reconstruct the first magnetic resonance image based on the magnetic resonance data after the super resolution processing, and reconstruct the second magnetic resonance image based on the magnetic resonance data so that the artifacts occurring by reconstruction with the super-resolution processing are suppressed.

Note 4.

The processing circuitry may execute the super-resolution processing with a first filter applied to the magnetic resonance data to reconstruct the first magnetic resonance image, and execute the super-resolution processing with a second filter having a stronger filter strength than the filter strength of the first filter applied to the magnetic resonance data to reconstruct the second magnetic resonance image.

Note 5.

The processing circuitry may execute the super-resolution processing with a first filter having a certain filter strength applied to the magnetic resonance data to reconstruct the first magnetic resonance image, and reconstruct the second magnetic resonance image based on the magnetic resonance data without using the super-resolution processing.

Note 6.

The processing circuitry may execute zero-filling on a no-signal high-frequency region outside the magnetic resonance data placed in a k-space as the super-resolution processing, and reconstruct the first magnetic resonance image based on the magnetic resonance data subjected to the zero-filling.

Note 7.

The processing circuitry may execute interpolation on a reconstructed image reconstructed based on the magnetic resonance data as the super-resolution processing to generate the first magnetic resonance image.

Note 8.

The interpolation may be the bicubic method or the Lanczos method.

Note 9.

The processing circuitry may execute interpolation on a reconstructed image reconstructed based on the magnetic resonance data as the super-resolution processing to generate the second magnetic resonance image.

Note 10.

The interpolation may be the bilinear method.

Note 11.

The first filter may be a weak filter reducing a strength of an end of a high-frequency region in the magnetic resonance data more weakly than a filter strength of the second filter or a non-filter passing the magnetic resonance data, and the high-frequency region may be a frequency region in which a contribution to edge information in the first magnetic resonance image is dominant.

Note 12.

The second filter may be a strong filter making a strength of an end of a high-frequency region in the magnetic resonance data stronger than a filter strength of the first filter and correspond to a low-pass filter having a stronger filter strength than the filter strength of the first filter, and the high-frequency region may be a frequency region in which a contribution to edge information in the first magnetic resonance image is dominant.

Note 13.

The first filter and the second filter may be smoothing filters.

Note 14.

The artifact may be an artifact generated by super-resolution processing.

Note 15.

The artifact may be a Gibbs artifact.

Note 16.

A magnetic resonance imaging apparatus comprising:
the medical image processing apparatus according to Note 2; and imaging control circuitry configured to collect the magnetic resonance data by magnetic resonance imaging on a subject.

Note 17.

A method of medical image processing comprising:
inputting a first magnetic resonance image reconstructed with super-resolution processing on magnetic resonance data and a second magnetic resonance image obtained by imaging the same object as the object of the first magnetic resonance image and with artifacts suppressed compared with the first magnetic resonance image, to a leaned model, the leaned model outputting a third magnetic resonance image having the same resolution as the resolution of the first magnetic resonance image and with the artifacts suppressed, and generating the third magnetic resonance image based on the first magnetic resonance image and the second magnetic resonance image, using the learned model.

Note 18.

A nonvolatile computer readable storage medium storing therein a medical image processing program comprising instructions that cause a computer to implement inputting a first magnetic resonance image reconstructed with super-resolution processing on magnetic resonance data and a second magnetic resonance image obtained by imaging the same object as the object of the first magnetic resonance image and with artifacts suppressed compared with the first magnetic resonance image, to a leaned model, the leaned model outputting a third magnetic resonance image having the same resolution as the resolution of the first magnetic resonance image and with the artifacts suppressed, and generating the third magnetic resonance image based on the first magnetic resonance image and the second magnetic resonance image, using the learned model.

What is claimed is:

1. A medical image processing apparatus comprising:
processing circuitry configured to
generate a first magnetic resonance image reconstructed with super-resolution processing on a magnetic resonance data,
generate a second magnetic resonance image reconstructed with super-resolution processing and filtering on the magnetic resonance data,
generate a third magnetic resonance image with suppressed artifacts based on the first magnetic resonance image and the second magnetic resonance image, using a learned model.

2. The medical image processing apparatus according to claim 1, wherein the processing circuitry
reconstructs the first magnetic resonance image based on the magnetic resonance data after the super-resolution processing, and
reconstructs the second magnetic resonance image based on the magnetic resonance data so that the artifacts occurring by reconstruction with the super-resolution processing are suppressed.

3. The medical image processing apparatus according to claim 2, wherein the processing circuitry
executes zero-filling on a no-signal high-frequency region outside the magnetic resonance data placed in a k-space as the super-resolution processing, and
reconstructs the first magnetic resonance image based on the magnetic resonance data subjected to the zero-filling.

4. The medical image processing apparatus according to claim 1, wherein the processing circuitry
executes the super-resolution processing with a first filter applied to the magnetic resonance data to reconstruct the first magnetic resonance image, and
executes the super-resolution processing with a second filter having a stronger filter strength than a filter strength of the first filter applied to the magnetic resonance data to reconstruct the second magnetic resonance image.

5. The medical image processing apparatus according to claim 4, wherein
the first filter is a weak filter reducing a strength of an end of a high-frequency region in the magnetic resonance data more weakly than a filter strength of the second filter or a non-filter passing the magnetic resonance data, and
the high-frequency region is a frequency region in which a contribution to edge information in the first magnetic resonance image is dominant.

6. The medical image processing apparatus according to claim 4, wherein
the second filter is a strong filter making a strength of an end of a high-frequency region in the magnetic resonance data stronger than a filter strength of the first filter and corresponds to a low-pass filter having a stronger filter strength than the filter strength of the first filter, and
the high-frequency region is a frequency region in which a contribution to edge information in the first magnetic resonance image is dominant.

7. The medical image processing apparatus according to claim 1, wherein the processing circuitry executes interpolation on a reconstructed image reconstructed based on the magnetic resonance data as the super-resolution processing to generate the first magnetic resonance image.

8. The medical image processing apparatus according to claim 1, wherein the processing circuitry executes interpolation on a reconstructed image reconstructed based on the magnetic resonance data as the super-resolution processing to generate the second magnetic resonance image.

9. A magnetic resonance imaging apparatus comprising:
the medical image processing apparatus according to claim 1; and
imaging control circuitry configured to collect the magnetic resonance data by magnetic resonance imaging on a subject.

10. A method of medical image processing comprising:
generating a first magnetic resonance image reconstructed with super-resolution processing on a magnetic resonance data,
generating a second magnetic resonance image reconstructed with super-resolution processing and filtering on the magnetic resonance data,
generating a third magnetic resonance image with suppressed artifacts based on the first magnetic resonance image and the second magnetic resonance image, using a learned model.

11. The method of medical image processing according to claim 10, further comprising:
reconstructing the first magnetic resonance image based on the magnetic resonance data after the super-resolution processing; and
reconstructing the second magnetic resonance image based on the magnetic resonance data so that the artifacts occurring by reconstruction with the super-resolution processing are suppressed.

12. The method of medical image processing according to claim 10, further comprising:
executing the super-resolution processing with a first filter applied to the magnetic resonance data to reconstruct the first magnetic resonance image; and
executing the super-resolution processing with a second filter having a stronger filter strength than a filter strength of the first filter applied to the magnetic resonance data to reconstruct the second magnetic resonance image.

13. A nonvolatile computer readable storage medium storing therein a medical image processing program comprising instructions that cause a computer to implement
generating a first magnetic resonance image reconstructed with super-resolution processing on a magnetic resonance data,
generating a second magnetic resonance image reconstructed with super-resolution processing and filtering on the magnetic resonance data,
generating a third magnetic resonance image with suppressed artifacts based on the first magnetic resonance image and the second magnetic resonance image, using a learned model.

14. The nonvolatile computer readable storage medium storing therein the medical image processing program comprising instructions according to claim 13 that cause the computer to further implement
reconstructing the first magnetic resonance image based on the magnetic resonance data after the super-resolution processing; and
reconstructing the second magnetic resonance image based on the magnetic resonance data so that the artifacts occurring by reconstruction with the super-resolution processing are suppressed.

* * * * *